(12) United States Patent
Wang et al.

(10) Patent No.: US 12,286,610 B2
(45) Date of Patent: Apr. 29, 2025

(54) BIOCULTURE MEAT DEVICE

(71) Applicant: China Meat Research Center, Beijing (CN)

(72) Inventors: Shouwei Wang, Beijing (CN); Feng Yang, Beijing (CN); Yingying Li, Beijing (CN); Shilei Li, Beijing (CN); Wenting Liu, Beijing (CN); Yushuang Li, Beijing (CN)

(73) Assignee: China Meat Research Center, Beijing (CN)

( * ) Notice: Subject to any disclaimer, the term of this patent is extended or adjusted under 35 U.S.C. 154(b) by 0 days.

(21) Appl. No.: 18/031,903

(22) PCT Filed: Aug. 5, 2022

(86) PCT No.: PCT/CN2022/110462
§ 371 (c)(1),
(2) Date: Apr. 14, 2023

(87) PCT Pub. No.: WO2023/016357
PCT Pub. Date: Feb. 16, 2023

(65) Prior Publication Data
US 2023/0383223 A1 Nov. 30, 2023

(30) Foreign Application Priority Data
Aug. 9, 2021 (CN) .......................... 202110906899.3

(51) Int. Cl.
*C12M 3/00* (2006.01)
*A23L 13/00* (2016.01)
(Continued)

(52) U.S. Cl.
CPC ............. *C12M 21/08* (2013.01); *A23P 30/10* (2016.08); *B01F 27/72* (2022.01); *C12M 27/02* (2013.01);
(Continued)

(58) Field of Classification Search
None
See application file for complete search history.

(56) References Cited

U.S. PATENT DOCUMENTS

2021/0145031 A1* 5/2021 Leung .................... C12M 29/10
2023/0407224 A1* 12/2023 Lavon .................... C12M 21/08

FOREIGN PATENT DOCUMENTS

| CN | 102489202 | 6/2012 |
|----|-----------|--------|
| CN | 109714962 | 5/2019 |

(Continued)

OTHER PUBLICATIONS

Guiling Dong, "Progress in Research on Cultured Meat and Relevant Patent Application" China Invention & Patent, vol. 16, No. 7, Jul. 31, 2019 (Jul. 31, 2019), pp. 71-75.
(Continued)

*Primary Examiner* — Holly Kipouros
(74) *Attorney, Agent, or Firm* — Bay State IP, LLC

(57) ABSTRACT

A bioculture meat device includes a culture medium conditioning tank (1), a cell proliferation tank (2), a muscle separating tank (3), a compression forming device (4), and a control system. The control system is divided into a culture medium regulation and control system (51) for controlling the culture medium conditioning tank (1), a cell proliferation control system (52) for controlling the cell proliferation tank (2), and a muscle collecting and shaping control system (53) for controlling the muscle separating tank (3) and the compression forming device (4). Different from traditional manual production, the device controls a culture environment through automatic equipment, realizes automatic integration from culturing to processing a finished product, improves the production capacity, and reduces the cost.

1 Claim, 6 Drawing Sheets

(51) Int. Cl.
    *A23P 30/10*     (2016.01)
    *B01F 27/72*     (2022.01)
    *C12M 1/00*     (2006.01)
    *C12M 1/06*     (2006.01)
    *C12M 1/34*     (2006.01)
    *B01F 101/06*     (2022.01)

(52) U.S. Cl.
    CPC ............ *C12M 29/04* (2013.01); *C12M 41/12* (2013.01); *C12M 41/34* (2013.01); *B01F 2101/06* (2022.01)

(56) References Cited

FOREIGN PATENT DOCUMENTS

| | | |
|---|---|---|
| CN | 110106077 | 8/2019 |
| CN | 112251352 | 1/2021 |
| CN | 113604359 | 11/2021 |
| WO | 2020123876 | 6/2020 |
| WO | 2021138674 | 7/2021 |

OTHER PUBLICATIONS

International Search Report, China National Intellectual Property Administration, Oct. 25, 2022.

\* cited by examiner

BIOCULTURE MEAT DEVICE

CROSS REFERENCE TO RELATED APPLICATION

This application is for entry into the U.S. National Phase from which priority is claimed under all applicable sections of Title 35 of the United States Code including, but not limited to, Sections 120, 363, and 365 (c) to International Application No. PCT/CN2022/110462 filed on Aug. 5, 2022, and which in turn claims priority under 35 USC 119 to Chinese Patent application Ser. No. 20/211,0906899.3 filed on Aug. 9, 2021.

TECHNICAL FIELD

The present disclosure relates to a bioculture meat device.

BACKGROUND

Bioculture meat is the closest to traditional meat among all types of artificial meat. It has all physical and chemical properties of real meat, so it has very high commercial value. Although being favored by the market, it is still produced manually due to the lack of professional production equipment, which makes it have huge production cost and extremely low yield.

SUMMARY

In view of the shortcomings of the abovementioned prior art, the present disclosure provides a device which can simulate a growth environment of myoblasts, promote the division and re-fusion of the myoblasts, and finally process a meat product, so as to reduce the production cost and improve the production capacity.

To solve the technical problem, the present disclosure adopts the technical solution that: a bioculture meat device includes a culture medium conditioning tank, a cell proliferation tank, a muscle separating tank, a compression forming device, and a control system. A first mixing blade is arranged in the culture medium conditioning tank. A pipeline connected to the top is arranged in the cell proliferation tank. The cell proliferation tank is provided with a culture medium inflow device connected to the culture medium conditioning tank. A plurality of culture panels are arranged outside the pipeline. The culture panels are hinged to the pipeline. A driving mechanism which makes the culture panels overturn up and down around hinge points is arranged on the pipeline. The bottom of the cell proliferation tank is arranged in a funnel shape. A first muscle collecting device connected to the cell proliferation tank is arranged in the pipeline. A second mixing blade is arranged below the pipeline and is driven by a second driving motor. The cell proliferation tank is provided with a temperature-controlled heating device. The muscle collecting device is connected to the muscle separating tank. A filter membrane layer is arranged in the muscle separating tank. A second muscle collecting device connected to the compression forming device is arranged above the filter membrane layer. A culture medium recovery device connected to the culture medium conditioning tank is arranged at the bottom of the muscle separating tank. Gas control devices and culture medium physical and chemical testing devices are arranged in the culture medium conditioning tank and the cell proliferation tank.

Further, the culture panels include a front panel, a rear panel, rotating shafts, and brackets. The brackets are hinged to both sides of the pipeline. A telescopic pulling rod is hinged to the top in the cell proliferation tank. An output shaft of the telescopic pulling rod is hinged to the first bracket below. An upper culture panel is connected to a lower culture panel through a stay wire.

Further, a rotating shaft is arranged on the bracket. The front panel and the rear panel are rotatably arranged on the rotating shaft. A shaft sleeve which realizes coaxial reverse rotation by fitting a gear is arranged on the rotating shaft. The rotating shaft and the shaft sleeve are respectively engaged with the front panel and the rear panel. The cell proliferation tank is provided with a first driving motor that drives the rotating shaft.

Further, a muscle stirring bin is arranged in the compression forming device. An extrusion worm that rotates through a third driving motor is arranged in the muscle stirring bin. The left end of the muscle stirring bin is connected to the second muscle collecting device and is provided with an auxiliary material inlet. A shaping mold is arranged at the right end of the muscle stirring bin.

The present disclosure has the beneficial effects that: different from traditional manual production, the bioculture meat device controls a culture environment through automatic equipment, realizes automatic integration from culturing to processing a finished product, improves the production capacity, and reduces the cost.

Figure 1:
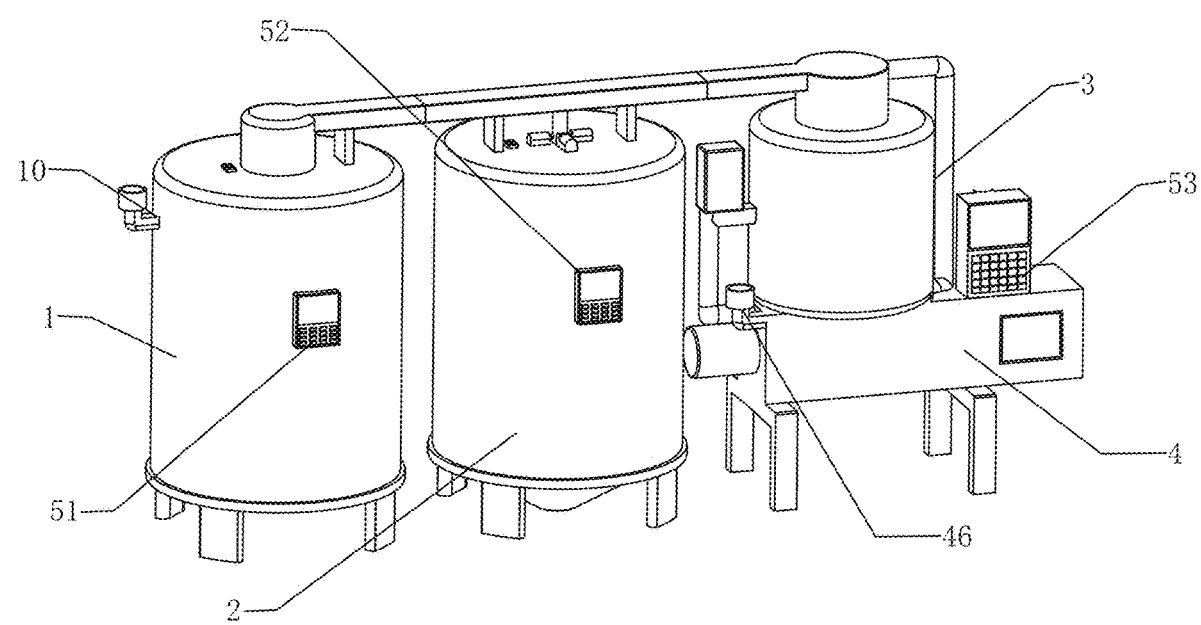
FIG. 1 is a schematic diagram of an overall structure of the present disclosure.

In the drawings: culture medium conditioning tank 1, cell proliferation tank 2, pipeline 21, culture medium inflow device 22, culture panel 23, stay wire 230, front panel 231, rear panel 232, rotating shaft 233, shaft sleeve 234, bracket 235, first gear 236, second gear 237, third gear 238, connecting gear 239, umbrella-shaped baffle 24, second mixing blade 25, second driving motor 251, flexible shaft 252, driving gear 253, first muscle collecting device 26, vacuum interlayer 27, telescopic pulling rod 28, first driving motor 29, flexible shaft 291, muscle separating tank 3, compression forming device 4, second muscle collecting device 41, muscle stirring bin 42, third driving motor 43, extrusion worm 44, stirring rod 45, auxiliary material inlet 46, shaping mold 47, culture medium regulation and control system 51, cell proliferation control system 52, and muscle collecting and shaping control system 53.

DETAILED DESCRIPTION OF THE EMBODIMENTS

In order to better understand the present disclosure, the implementation mode of the present disclosure will be explained in detail in combination with FIG. 1 to FIG. 5.

It is to be noted that the following front, rear, left, right, up and down are subject to the front, rear, left, right, up and down shown in FIG. 1.

A bioculture meat device of the present disclosure includes a culture medium conditioning tank 1, a cell proliferation tank 2, a muscle separating tank 3, a compression forming device 4, and a control system. The control system is divided into a culture medium regulation and control system 51 for controlling the culture medium conditioning tank 1, a cell proliferation control system 52 for controlling the cell proliferation tank 2, and a muscle collecting and shaping control system 53 for controlling the muscle separating tank 3 and the compression forming device 4.

Figure 2:
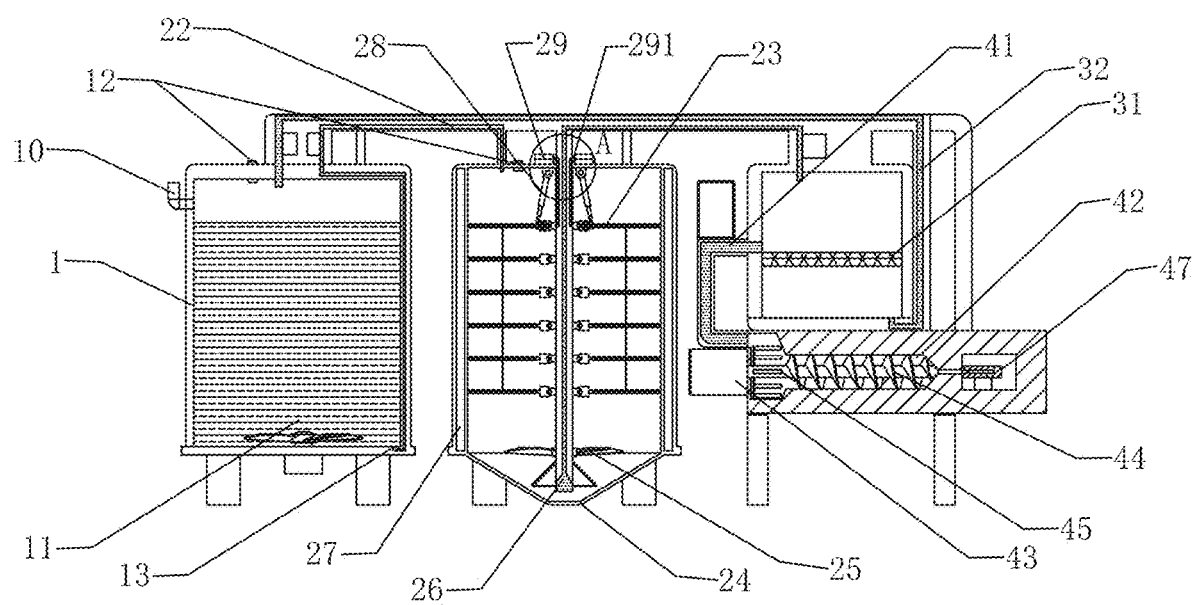
FIG. 2 is a schematic diagram of an internal structure of the present disclosure.

As shown in FIG. 1 and FIG. 2, the culture medium conditioning tank 1 is provided with an injection port 10 used for injecting a culture medium, and is provided with a valve. A first mixing blade 11 used for mixing a culture medium is rotatably arranged in the culture medium conditioning tank 1. A pipeline 21 connected to the top in the culture medium conditioning tank 1 is arranged in the cell proliferation tank 2. A culture medium inflow device 22 connected to the culture medium conditioning tank 1 is arranged in the culture medium conditioning tank 1. A plurality of culture panels 23 are arranged outside the pipeline 21. The culture panels are hinged to the pipeline 21. A driving mechanism which makes the culture panels 23 overturn up and down around hinge points is arranged on the pipeline 21. The bottom of the cell proliferation tank 2 is arranged in a funnel shape, which facilitates the collection of muscle tissues.

Figure 3:
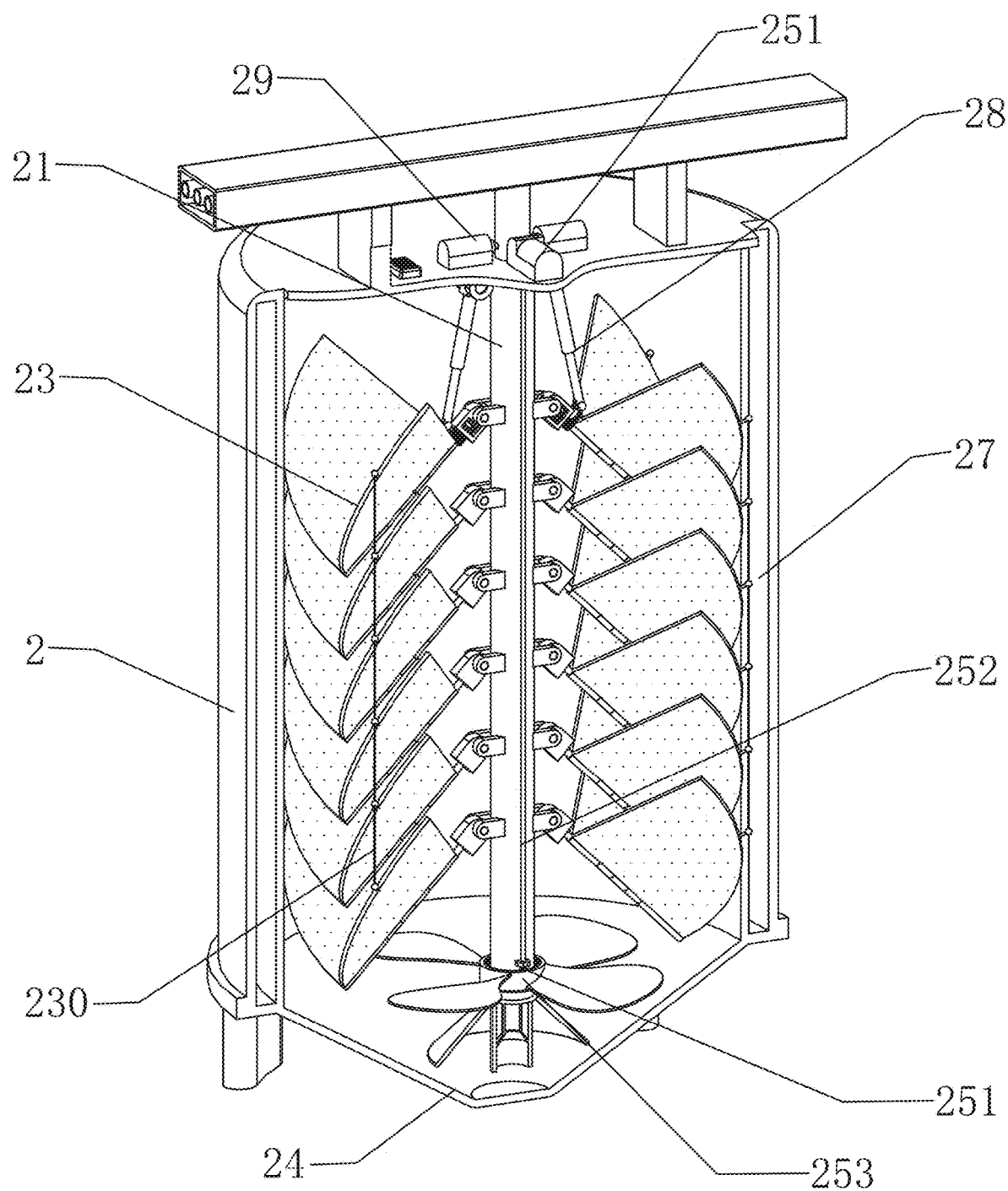
FIG. 3 is a diagram of an internal structure of a cell proliferation tank after being cut.

Inoculated cells in the culture medium flowing into the cell proliferation tank 2 are at different positions, the concentration of the cells at different layers is different, and the meanwhile, the newly added cells need to be mixed in the culture medium, so that a second mixing blade 25 is rotatably arranged below the pipeline 21, which is responsible for secondary mixing of the culture medium. As shown in FIG. 3, the second mixing blade 25 is rotatably arranged at the bottom of the pipeline 21. An internal gear is annularly arranged at the bottom of the second mixing blade 25. A driving gear 253 matched with the internal gear is driven by using a second driving motor 251 through a flexible shaft 252, so as to drive the second mixing blade 25. A first muscle collecting device 26 connected to the cell proliferation tank 2 is arranged in the pipeline 21. The cell proliferation tank 2 is provided with a vacuum interlayer 27 for insulating heat, and is provided with a temperature-controlled heating device. Gas control devices 12 and culture medium physical and chemical testing devices 13 are arranged in the culture medium conditioning tank 1 and the cell proliferation tank 2. The culture medium physical and chemical testing device 13 is responsible for detecting the condition of the culture medium. Corresponding control systems control the gas control devices 12 and the temperature-controlled heating devices to correspondingly regulate the temperature and the gas inside. The gas control device 12 in the cell proliferation tank 2 can detect the data, such as the dissolved oxygen, the carbon dioxide concentration, and real-time pressure intensity of the culture medium in real time, and upload the data to the cell proliferation control system 51.

A first muscle collecting device 26 is connected to the top in the muscle separating tank 3. An umbrella-shaped baffle 24 is arranged at the bottom of the pipeline 21, and is used for reducing the influence of the second mixing blade 25 on the first collecting device 26 at the bottom of the cell proliferation tank 2.

Figure 5:
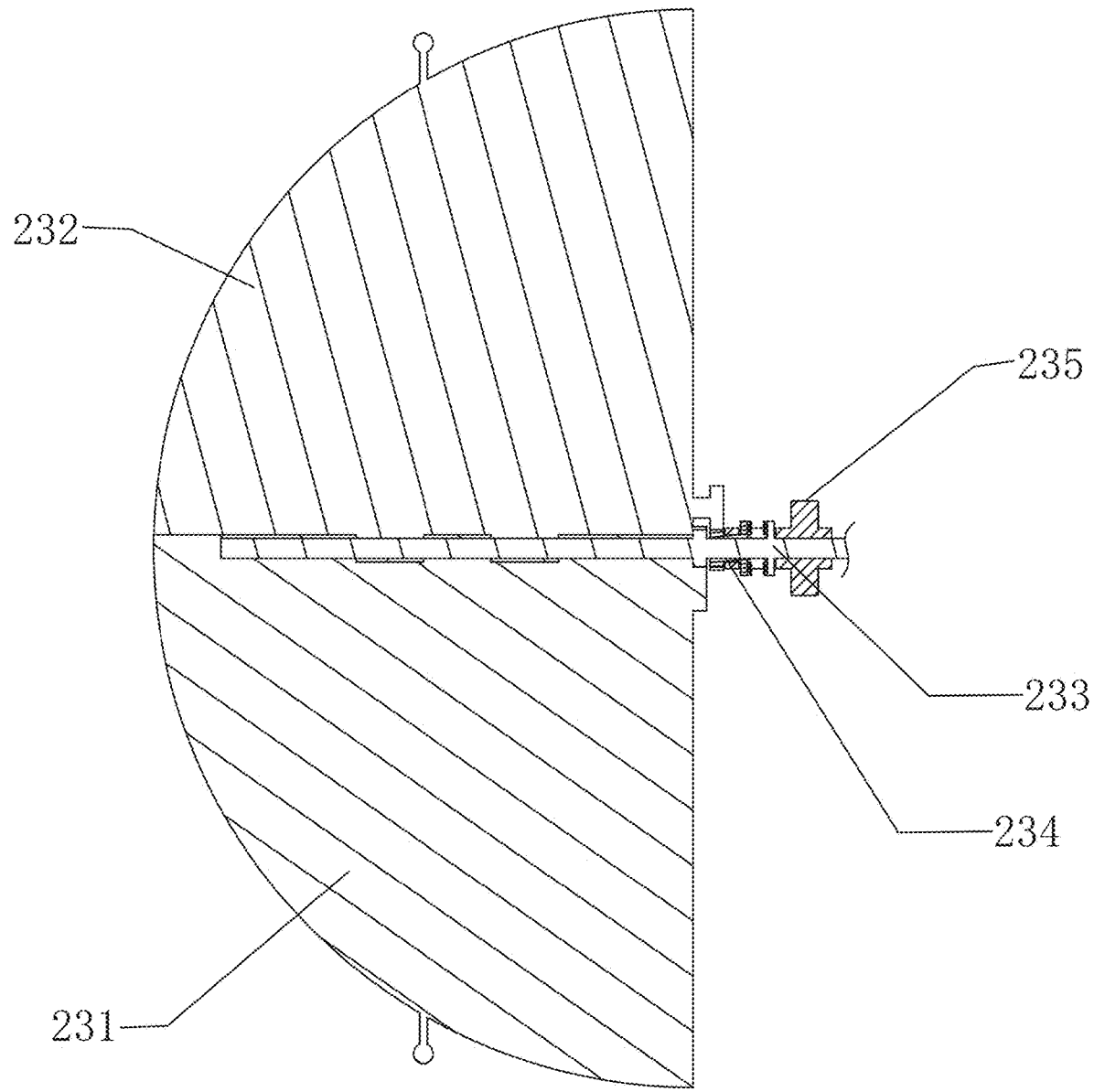
FIG. 5 is a sectional view of a top surface of the culture panel.
Figure 6:
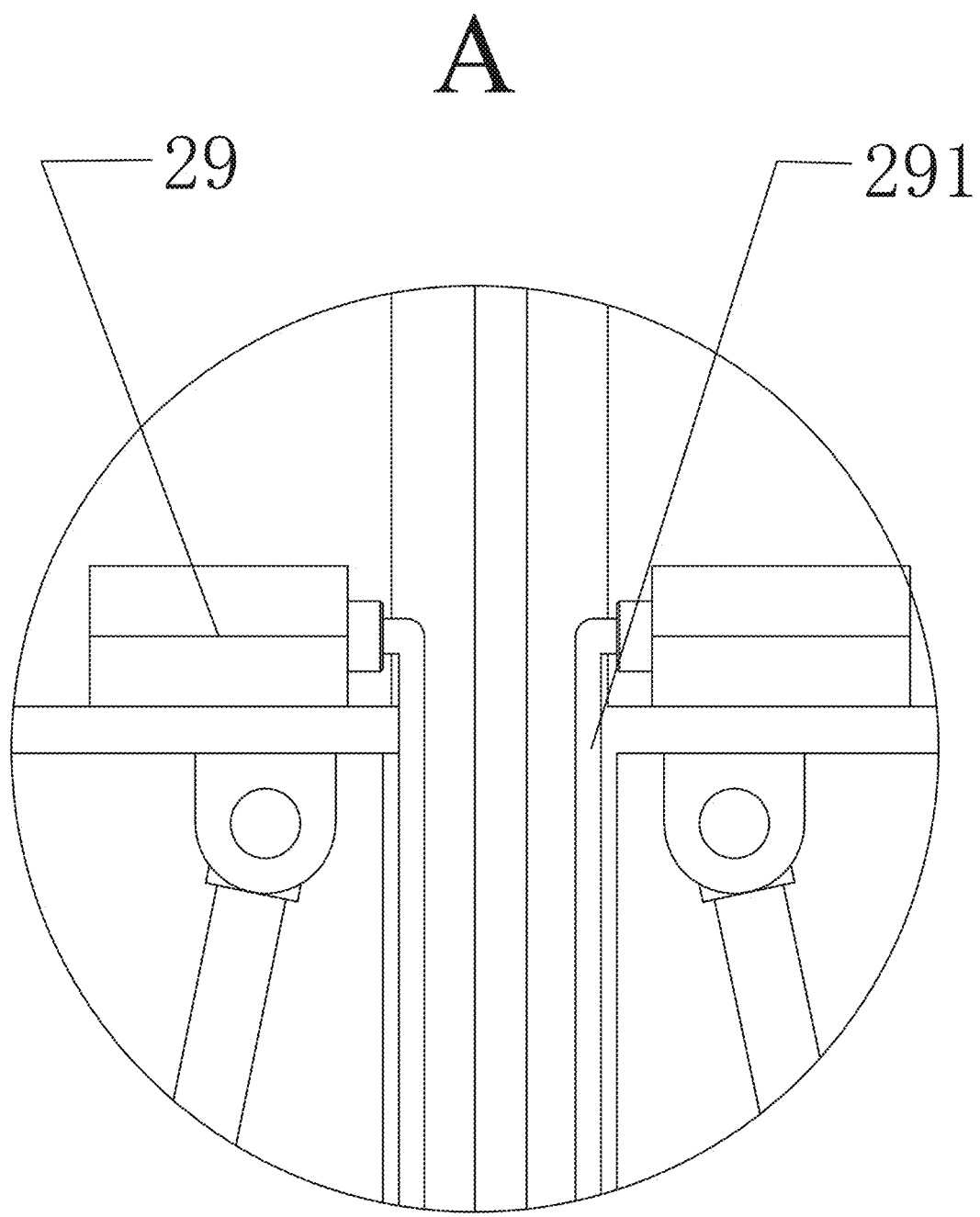
FIG. 6 is an enlarged detail of part A of FIG. 2.

A filter membrane used for filtering muscle tissues is arranged in the muscle separating tank 3. A protein membrane may be used to make a filter membrane layer 31 to separate the muscle tissues from the culture medium. A second muscle collecting device 41 of the compression forming device 4 is arranged on the filter membrane layer 31. A culture medium recovery device 32 connected to the interior of the culture medium conditioning tank 1 is arranged at the bottom of the muscle separating tank 3. As shown in FIG. 5, a muscle stirring bin 42 is arranged in the compression forming device 4. An extrusion worm 44 which rotates through a third driving motor 43 is arranged in the muscle stirring bin 42. A stirring rod 45 is arranged on the left side of the extrusion worm 44. The left end of the muscle stirring bin 42 is connected to the second muscle collecting device 41 and is provided with an auxiliary material inlet 46 used for adding an auxiliary material, such as pigment. A shaping mold 47 is arranged at the right end of the muscle stirring bin 42. When the extrusion worm 44 rotates, the muscle tissues input into the muscle stirring bin 42 by the second muscle collecting device 41 will be gradually injected into the shaping mold 47 by the extrusion worm 44.

The culture medium inflow device 22 and the culture medium recovery device 32 are water pipes with water pumps. The used water pipes are fully distributed with micro-pores, which reduces the influence on cells caused by over high flow rate. The first muscle collecting device 26 and the second muscle collecting device 41 are absorption pipelines with centrifugal turbines. Flow regulating valves for controlling the flow are respectively arranged between the culture medium inflow device 22 and the culture medium recovery device 32 and between the first muscle collecting device 26 and the second muscle collecting device 41.

Figure 4:
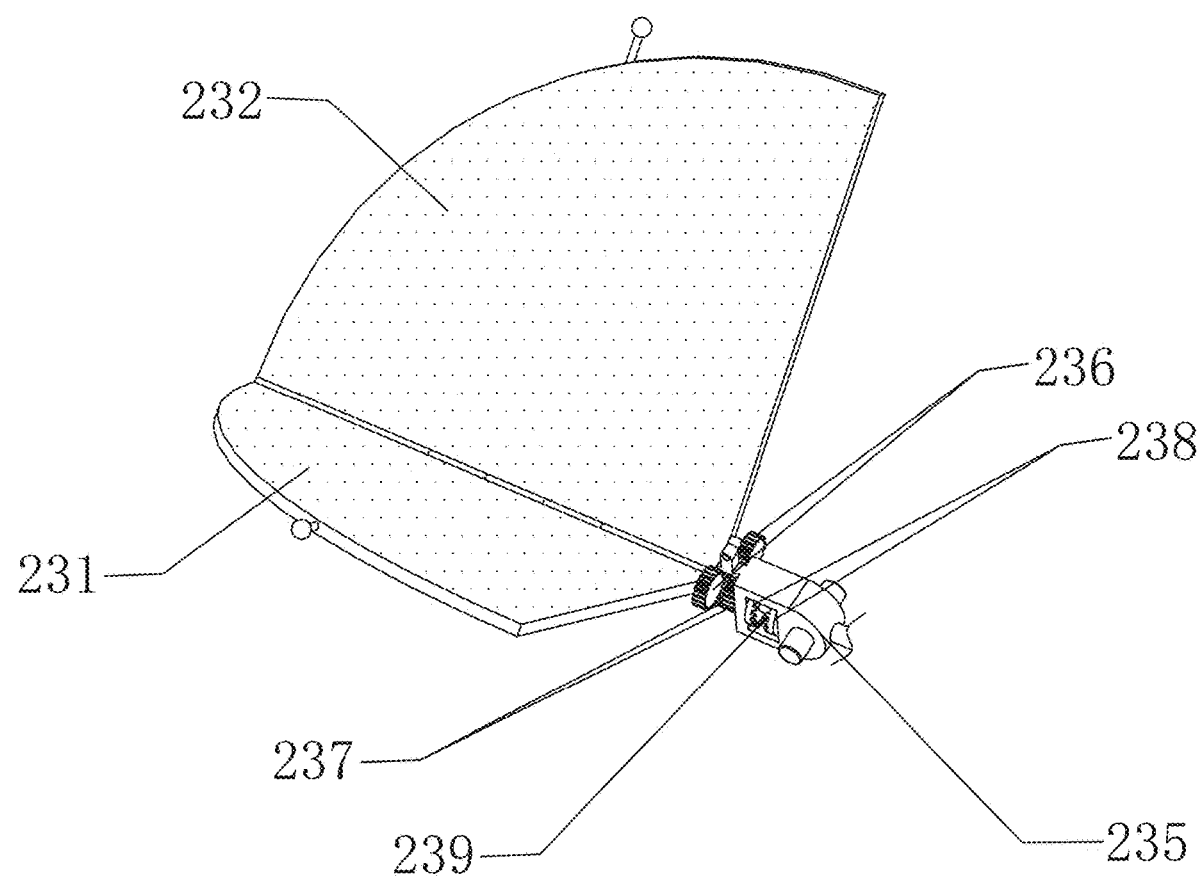
FIG. 4 is a schematic structural diagram of a culture panel.

As shown in FIG. 3 and FIG. 4, the culture panels 23 include a front panel 231, a rear panel 232, rotating shafts 233, shaft sleeves 234, and brackets 235. The brackets 235 are hinged to both sides of the pipeline 21. A telescopic pulling rod 28 is hinged to the top in the cell proliferation tank 2. An output shaft of the telescopic pulling rod 28 is hinged to a bracket 235. The rotating shaft 233 is rotatably arranged on the bracket 235. The front panel 231 and the rear panel 232 are rotatably arranged on the rotating shaft 233. A first gear 236 is arranged on each of the front panel 231 and the rear panel 232. The shaft sleeve 234 is rotatably arranged on the rotating shaft 233. Second gears 237 and third gears 238 are respectively arranged on the left side and the right side of the rotating shaft 233 and the shaft sleeve 234. The two second gears 237 are respectively engaged with the two first gears 236. The two third gears 238 are driven and connected by a connecting gear 239 arranged on the bracket 235. A first driving motor 29 is arranged at the top of the cell proliferation tank 2. The first driving motor 29 is connected to the rotating shaft 233 and drives the same through a flexible shaft 291. The front panels 231 adjacent to each other up and down are connected through a stay wire 230. The rear panels 232 adjacent to each other up and down are also connected through a stay wire 230.

When the rotating shaft 233 rotates, the third gears 238 on the rotating shaft 233 and the shaft sleeve 234 will realize coaxial reverse rotation through the connecting gear 239. During this period, the two second gears 237 on the rotating shaft 233 and the shaft sleeve 234 will be engaged with each other because of the two first gears 236 on the front panel 231 and the rear panel 232, so that the front panel 231 and the rear panel 232 are folded in half up and down on the rotating shaft 233. The telescopic pulling rod 28 between the bracket 235 and the cell proliferation tank 2 retracts or stretches or is opened, so that the overall culture panels 23 overturns up and down around the hinge points of the brackets 235 and the pipeline 21. The culture panels 23 that are adjacent to each other up and down are connected through two stay wires 230. When the uppermost culture panel 23 is folded in half or rotates reversely, other culture panels 23 below will move synchronously.

The culture panels 23 are made of a material with good hydrophilicity and high biocompatibility. Other structures that are in contact with the muscle tissues and the culture medium are all made of hydrophobic materials.

When the bioculture meat device is used, raw materials (a PH buffer solution, serum, a growth factor, a myogenic factor, a culture medium, etc.) for producing bioculture meat are added into the culture medium conditioning tank in proportion first, and then, the raw materials are rotated by the first mixing blade controlled by the culture medium regulation and control system to produce the culture medium. Then, the culture medium is injected into the cell proliferation tank through the culture medium inflow device. Next, the cell proliferation control system controls the cooperation between the temperature-controlled heating device and the gas control device, and simulates an in-vivo biological environment suitable for the proliferation of myoblasts, so that the cells in the culture medium proliferate on the culture panels. When the cells proliferate to a certain amount, the cell proliferation control system will control the retracting and stretching and the first driving motor folds the overall culture medium panel in half and then tilts it downward, so as to gather the cells. Under the action of the biological factor in the culture medium conditioning tank, the myoblasts are promoted to be fused into myotubes and to further form muscle tissues. Then the muscle tissues slowly slide into a collecting device, and then the first muscle collecting device extracts the muscle tissues into the muscle separating tank. The muscle tissues entering the muscle separating tank will flow into a filtered culture medium with the filter membrane, so that the culture medium flows into the culture medium conditioning tank again through the culture medium recovery device. The filtered muscle tissues will be transported into the stirring bin of the compression forming device through the second muscle collecting device. During this period, auxiliary materials, such as condiments, may be added in the auxiliary material inlet. The muscle tissues and the condiments may be mixed by the stirring rod at the left end of the rotating extrusion worm. Then, the muscle tissues in the stirring bin will be transported into the shaping mold by using the worm, and the muscle tissues are extruded into a finished product after being injected into the shaping mold.

In the overall process, the culture medium conditioning tank and the culture medium control system are in responsible for regulating the compositions of the culture medium in different periods of culture meat production. For example, a cell growth promoting factor is delivered in a cell proliferation period, and a myogenic factor is delivered in a muscle fiber formation period, so as to control the production process of culture meat. Meanwhile, intracellular toxin will also be removed from the culture medium after the secondary recovery, and a new cell factor and cell culture compositions are delivered, so as to realize the reuse and renewable repeated applications of the culture medium.

The cell proliferation tank and the cell proliferation control system are in responsible for promoting the proliferation cells through unfolded culture panels, and promoting the fusion of cellular myotubes and the generation of muscle fibers by using micro-gravity through the folded culture panels, thereby promoting the production of muscle micro-tissues.

The muscle separating tank, the compression forming device, and the muscle shaping control system are in responsible for separating the micro-tissues of the culture medium from the culture medium, and forming, toning, shaping, and mixing the micro-tissues of the culture meat. Finally, a finished culture meat product is formed.

What is claimed is:

1. A bioculture meat device, comprising a culture medium conditioning tank, a cell proliferation tank, a muscle separating tank, a compression forming device, and a control system, wherein a first mixing blade is arranged in the culture medium conditioning tank; a pipeline connected to a top of the culture medium conditioning tank is arranged in the cell proliferation tank; the cell proliferation tank is provided with a culture medium inflow device connected to the culture medium conditioning tank; a plurality of culture panels are arranged outside the pipeline; the culture panels are hinged to the pipeline; a driving mechanism that makes the culture panels overturn up and down around hinge points is arranged on the pipeline; a bottom of the cell proliferation tank is arranged in a funnel shape; a first muscle collecting device connected to the cell proliferation tank is arranged in the pipeline; a second mixing blade is rotatably arranged below the pipeline; the cell proliferation tank is provided with a temperature-controlled heating device; the first muscle collecting device is connected to a top of the muscle separating tank; a filter membrane layer is arranged in the muscle separating tank; second muscle collecting device connected to the compression forming device is arranged above the filter membrane layer; a culture medium recovery device connected to the culture medium conditioning tank is arranged at a bottom of the muscle separating tank; gas control devices and culture medium physical and chemical testing devices are arranged in the culture medium conditioning tank and the cell proliferation tank;

the culture panels comprise a front panel, a rear panel, a rotating shaft, and brackets; the brackets are hinged to two sides of the pipeline; a telescopic pulling rod is hinged to a top in the cell proliferation tank; an output shaft of the telescopic pulling rod is hinged to a first bracket of the brackets below the telescopic pulling rod; an upper culture panel is connected to a lower culture panel through a stay wire;

the rotating shaft is arranged on the brackets; the front panel and the rear panel are rotatably arranged on the rotating shaft; a shaft sleeve that realizes coaxial reverse rotation by fitting a gear is arranged on the rotating shaft; the rotating shaft and the shaft sleeve are respectively engaged with the front panel and the rear panel; the cell proliferation tank is provided with a first driving motor that drives the rotating shaft; and the second mixing blade is driven by a second driving motor; and a muscle stirring bin is arranged in the compression forming device; an extrusion worm that rotates through a third driving motor is arranged in the muscle stirring bin; a left end of the muscle stirring bin is connected to the second muscle collecting device and is provided with an auxiliary material inlet; and a shaping mold is arranged at a right end of the muscle stirring bin.

\* \* \* \* \*